US008754035B2

(12) United States Patent
Chen (10) Patent No.: US 8,754,035 B2
(45) Date of Patent: *Jun. 17, 2014

(54) COMPOSITIONS AND METHODS FOR VISUALIZING AND ELIMINATING CANCER STEM CELLS

(75) Inventor: Wen Y. Chen, Greer, SC (US)

(73) Assignee: Oncolix, Inc., Houston, TX (US)

( * ) Notice: Subject to any disclaimer, the term of this patent is extended or adjusted under 35 U.S.C. 154(b) by 553 days.

This patent is subject to a terminal disclaimer.

(21) Appl. No.: 12/706,702

(22) Filed: Feb. 16, 2010

(65) Prior Publication Data

US 2010/0215577 A1  Aug. 26, 2010

Related U.S. Application Data (60) Provisional application No. 61/155,624, filed on Feb. 26, 2009.

(51) Int. Cl.
*A61K 38/00* (2006.01)
*C07K 7/06* (2006.01)

(52) U.S. Cl.
USPC ........... 514/1.1; 514/2.1; 514/19.3; 514/19.4; 514/21.2; 530/388.22

(58) Field of Classification Search
None
See application file for complete search history.

(56) References Cited

U.S. PATENT DOCUMENTS

| | | | |
|---|---|---|---|
| 7,001,888 B2 | 2/2006 | Tidmarsh et al. | |
| 7,115,556 B2 | 10/2006 | Chen et al. | |
| 7,422,899 B2 | 9/2008 | Eienbaas et al. | |
| 7,425,535 B2 | 9/2008 | Yu et al. | |
| 2003/0022833 A1 | 1/2003 | Chen et al. | |
| 2004/0136952 A1 | 7/2004 | Bhaskaran et al. | |
| 2005/0238628 A1 | 10/2005 | Blau | |
| 2005/0271626 A1* | 12/2005 | Chen et al. | 424/93.2 |
| 2007/0060520 A1 | 3/2007 | Chen et al. | |
| 2007/0160534 A1 | 7/2007 | Dennis et al. | |
| 2010/0303719 A1 | 12/2010 | Huang et al. | |

FOREIGN PATENT DOCUMENTS

| | | |
|---|---|---|
| DE | 2646854 C2 | 5/1977 |
| DE | 2616086 C2 | 11/1977 |
| EP | 1398322 B1 | 4/2006 |
| WO | 99/58142 | 11/1999 |

OTHER PUBLICATIONS

NCI cancer fact sheet.*
Ginestier et al. Cell Stem Cell 2007.*
Wicha Clin Cancer Res 2006.*
Asai-Sato et al. Int. J Cancer 2005.*
Tuefferd PloS ONE 2007.*
Metastatic cancer, pp. 1-16 NCI cancer fact sheet, May 23, 2011.*
Bontenbal, M., et al. "Feasibility, Endocrine and Anti-Tumour Effects of a Triple Endocrine Therapy with Tamoxifen, a Somatostatin Analogue and an Antiprolacatin in Post-Menopausal Metastatic Breast Cancer: A Randomized Study with Long-Term Follow-Up," British Journal of Cancer, vol. 77, No. 1, pp. 115-122 (1998).
Scotti, M., et al., "Additive effects of a Prolactin Receptor Antagonist, G129R, and Herceptin on Inhibition of HER2-Overexpressing Breast Cancer Cells," Breast Cancer Res. Treat., vol. 111, pp. 241-250 (2008).
Bhattacharyya, S., et al., "Synthesis and Evaluation of Near-Infrared (NIR) Dye-Hercepptin Conjugates as Photoacoustic Computed Tomography (PCT) Probes for HER2 Expression in Breast Cancer," Bioconjugate Chem., vol. 19, pp. 1186-1193 (2008).
Tian, X., et al., "Clinicopathologic and Prognostic Characteristics of Triple-Negative Breast Cancer," Onkologle, vol. 31, pp. 610-614 (2008).
Partial International Search Report of PCT/US2010/024340 dated Sep. 16, 2010.
Pierce, S., et al., "Quantification of Prolactin Receptor mRNA in Multiple Human Tissues and Cancer Cell Lines by Real Time RT-PCT," Journal of Endocrinology, vol. 171, pp. R1-R4 (2001).
Harbaum, L., et al., "Clinicopathological Significance of Prolactin Receptor Expression in Colorectal Carcinoma and Corresponding Metastases," Modern Pathology, vol. 23, pp. 961-971 (2010) Abstract.
Asai-Sato, Mikiko, et al., "Prolactin Inhibits Apoptosis of Ovarian Carcinoma Cells Induced by Serum Starvation or Cisplatin Treatment," Int. J. Cancer, vol. 115, pp. 539-544 (2005).
Dunyong, T., et al., "Evidence supporting a role for prolactin in the progression of ovarian cancer", and "Evidence supporting a role for prolactin in the progression of ovarian cancer", Proceedings of the American Association for Cancer Research Annual Meeting vol. 50, p. 191 (Apr. 2009), & 100th Annual Meeting of the American-Association-For-Cancer-Research Denver, CO, Apr. 18-22, 2009.
International Preliminary Report on Patentability of PCT/US2010/024340 dated Aug. 30, 2011.
International Preliminary Report on Patentability of PCT/US2011/061040 dated May 21, 2013.
International Search Report of PCT/US2010/024340 dated Dec. 28, 2010.
International Search Report of PCT/US2011/061040 dated Mar. 9, 2012.
Jacobson, E., et al., "Unexploited therapies in breast and prostate cancer: blockade of the prolactin receptor", Trends in Endocrinology and Metabolism, vol. 21, No. 11, pp. 691-698 (Sep. 16, 2010).
U.S. Appl. No. 12/948,329—Restriction Requirement dated Oct. 2, 2012.
U.S. Appl. No. 12/948,329—Non-final office action dated Apr. 11, 2013.

* cited by examiner

*Primary Examiner* — James H Alstrum Acevedo
*Assistant Examiner* — Li Lee
(74) *Attorney, Agent, or Firm* — Morgan Lewis & Bockius LLP (57) ABSTRACT

The present invention relates generally to the field of cancer diagnosis and treatment, and more particularly to compositions and methods that may be useful for eliminating cancer cells with stem-like characteristics. The disclosed compositions and methods may also be useful for managing breast cancer, ovarian cancer, cervical cancer or endometrial (uterine) cancer with metastases; and visualizing the cancer cells in patient's body. The compositions of the instant invention include human prolactin receptor antagonist G129R.

11 Claims, 9 Drawing Sheets

```
<160> NUMBER OF SEQ ID NOS: 39

<210> SEQ ID NO 1
<211> LENGTH: 199
<212> TYPE: PRT
<213> ORGANISM: Homo sapiens

<400> SEQUENCE: 1
```

| | | | | | | | | | | | | | | |
|---|---|---|---|---|---|---|---|---|---|---|---|---|---|---|
| Leu | Pro | Ile | Cys | Pro | Gly | Gly | Ala | Ala | Arg | Cys | Gln | Val | Thr | Leu | Arg |
| 1 | | | | 5 | | | | | 10 | | | | | 15 | |
| Asp | Leu | Phe | Asp | Arg | Ala | Val | Val | Leu | Ser | His | Tyr | Ile | His | Asn | Leu |
| | | | 20 | | | | | 25 | | | | | 30 | | |
| Ser | Ser | Glu | Met | Phe | Ser | Glu | Phe | Asp | Lys | Arg | Tyr | Thr | His | Gly | Arg |
| | | 35 | | | | | 40 | | | | | 45 | | | |
| Gly | Phe | Ile | Thr | Lys | Ala | Ile | Asn | Ser | Cys | His | Thr | Ser | Ser | Leu | Ala |
| | 50 | | | | | 55 | | | | | 60 | | | | |
| Thr | Pro | Glu | Asp | Lys | Glu | Gln | Ala | Gln | Gln | Met | Asn | Gln | Lys | Asp | Phe |
| 65 | | | | | 70 | | | | | 75 | | | | | 80 |
| Leu | Ser | Leu | Ile | Val | Ser | Ile | Leu | Arg | Ser | Trp | Asn | Glu | Pro | Leu | Tyr |
| | | | | 85 | | | | | 90 | | | | | 95 | |
| His | Leu | Val | Thr | Glu | Val | Arg | Gly | Met | Gln | Glu | Ala | Pro | Glu | Ala | Leu |
| | | | 100 | | | | | 105 | | | | | 110 | | |
| Leu | Ser | Lys | Ala | Val | Glu | Ile | Glu | Glu | Gln | Thr | Lys | Arg | Leu | Leu | Arg |
| | | 115 | | | | | 120 | | | | | 125 | | | |
| Gly | Met | Glu | Leu | Ile | Val | Ser | Gln | Val | His | Pro | Glu | Thr | Lys | Glu | Asn |
| | 130 | | | | | 135 | | | | | 140 | | | | |
| Glu | Ile | Tyr | Pro | Val | Trp | Ser | Gly | Leu | Pro | Ser | Leu | Gln | Met | Ala | Asp |
| 145 | | | | | 150 | | | | | 155 | | | | | 160 |
| Glu | Glu | Ser | Arg | Leu | Ser | Ala | Tyr | Tyr | Asn | Leu | Leu | His | Cys | Leu | Arg |
| | | | | 165 | | | | | 170 | | | | | 175 | |
| Arg | Asp | Ser | His | Lys | Ile | Asp | Asn | Tyr | Leu | Lys | Leu | Leu | Lys | Cys | Arg |
| | | | 180 | | | | | 185 | | | | | 190 | | |
| Ile | Ile | His | Asn | Asn | Asn | Cys | | | | | | | | | |
| | | | 195 | | | | | | | | | | | | |

SEQ ID NO: 4

COMPOSITIONS AND METHODS FOR VISUALIZING AND ELIMINATING CANCER STEM CELLS

CROSS-REFERENCE TO RELATED APPLICATIONS

This application claims the benefit of U.S. Provisional Application No. 61/155,624, filed Feb. 26, 2009, the contents of which are incorporated herein by reference.

FIELD OF THE INVENTION

The present invention relates generally to the field of cancer diagnosis and treatment, and more particularly to compositions and methods that are useful in eliminating HER2+ breast cancer cells, triple-negative breast cancer cells that do not express estrogen receptor, progesterone receptor or HER2/neu, and cancer cells with stem-like characteristics. The compositions and methods of the instant invention may also be useful for managing metastatic breast cancer, and visualizing breast cancer cells in patient's body.

BACKGROUND OF THE INVENTION

Breast cancers are divided into subtypes based on whether they express estrogen receptor, progesterone receptor and Her2/neu. Before cancer treatment is commenced, it is important to identify patient's cancer subtype because some drugs target cancer cells that express estrogen receptor, while other drugs target cancer cells that express other receptors. The HER2/neu gene has been implicated in mammary tumorigenesis, tumor growth and metastasis. HER2/neu is amplified in 20-30% of human breast cancers and the HER2-positive subtype of breast cancer is associated with aggressive metastatic disease. (Korkaya et al. 2008. *Oncogene*). The instant invention may be helpful in treating HER2-positive breast cancers by providing new compositions and methods that can be used for eliminating HER2-positive breast cancer cells.

Recently a new subtype of breast cancer cells has been identified. These cancer cells are called triple-negative breast cancer cells because they do not express estrogen receptor, progesterone receptor or Her2/neu. (Dent et al. 2007. *Clinical Cancer Research* 13: 4429-4434). According to Cancer Research UK (2007), triple-negative breast cancer cases make up approximately 15% of all breast cancer cases. In comparison to other known breast cancer subtypes, the triple-negative subtype is more aggressive, less responsive to standard treatment and is associated with poorer overall patient prognosis. (Dent et al. 2007. *Clinical Cancer Research* 13: 4429-4434). Thus, there remains the need for compositions and methods to diagnose and treat triple-negative breast cancer patients.

Recent studies suggest that a wide variety of cancers, including breast cancer, arise from a small subset of cancer stem cells (CSCs) through deregulation of self-renewal pathways. It has been reported that a sub-population of breast cancer cells with stem cell-like characteristics is CD44 and CD133 positive, CD24 negative and expresses aldehyde dehydrogenase 1 (ALDH1). (Crocker et al. 2008. J Cell Mol Med). There remains the need for compositions and methods that identify and eradicate a sub-population of breast cancer cells with stem cell-like characteristics.

Prolactin ("PRL") is a 23-kDa neuroendocrine hormone which is structurally related to growth hormone and, to a lesser degree, to members of the interleukin family (Reynolds et al., 1997, Endocrinol. 138:5555-5560, Cunningham et al., 1990, Science 247:1461-1465; Wells et al., 1993, Recent Prog. Horm. Res. 48:253-275). Prolactin receptors are present in the mammary glands, ovaries, pituitary glands, heart, lung, thymus, spleen, liver, pancreas, kidney, adrenal gland, uterus, skeletal muscle, skin and areas of the central nervous system. Mancini T. (2008), "Hyperprolactinemia and Prolactinomas," *Endocrinology & Metabolism Clinics of North America* 37: 67. When prolactin binds to its receptor it causes it to dimerize with another prolactin receptor, which results in the activation of Janus kinase 2, a tyrosine kinase that initiates the JAK-STAT pathway. The activation of the prolactin receptor also results in the activation of mitogen-activated protein kinases and Src kinase mitogen. Mancini, T. (2008). "Hyperprolactinemia and Prolactinomas," *Endocrinology & Metabolism Clinics of North America* 37: 67. "Prolactin receptor antagonist" refers to a form of prolactin that interferes with the prolactin signaling pathway. Such prolactin receptor antagonists have been previously described in US Patent Application 2007/0060520 to inventors W. Chen and T. Wagner.

SUMMARY OF THE INVENTION

The instant invention provides a method for inhibiting growth of breast carcinoma triple-negative cells that do not express estrogen receptor, progesterone receptor or Her2/neu in a patient, which comprises administering to the patient a human prolactin receptor antagonist. The human prolactin receptor antagonists useful in the method include those in which glycine at position 129 is substituted with another amino acid, such as, for example, arginine. Other human prolactin receptor antagonists useful in the method include those in which glycine at position 129 is substituted with any of the following amino acids: valine, leucine, isoleucine, serine, threonine, proline, tyrosine, cysteine, methionine, arginine, histidine, tryptophan, phenylalanine, lysine, asparagine, glutamine, aspartic acid or glutamic acid.

In yet other embodiments, the instant invention provides a method for inhibiting development of metastases in a breast cancer patient, which comprises administering to the patient a human prolactin receptor antagonist. The human prolactin receptor antagonists useful in the method include those in which glycine at position 129 is substituted with another amino acid, such as, for example, arginine. Other human prolactin receptor antagonists useful in the method include those in which glycine at position 129 is substituted with any of the following amino acids: valine, leucine, isoleucine, serine, threonine, proline, tyrosine, cysteine, methionine, arginine, histidine, tryptophan, phenylalanine, lysine, asparagine, glutamine, aspartic acid or glutamic acid.

The instant invention also concerns a method for decreasing the activity of aldehyde dehydrogenase 1 (ALDH1) in a breast cancer patient, which comprises administering to the patient a human prolactin receptor antagonist. The human prolactin receptor antagonists useful in the method include those in which glycine at position 129 is substituted with another amino acid, such as, for example, arginine. Other human prolactin receptor antagonists useful in the method include those in which glycine at position 129 is substituted with any of the following amino acids: valine, leucine, isoleucine, serine, threonine, proline, tyrosine, cysteine, methionine, arginine, histidine, tryptophan, phenylalanine, lysine, asparagine, glutamine, aspartic acid or glutamic acid.

The instant invention also concerns a method for decreasing the number of cancer stem cells in a breast cancer patient, which comprises administering to the patient a human prolactin receptor antagonist. The human prolactin receptor antagonists useful in the method include those in which a glycine at position 129 is substituted with another amino acid, such as, for example, arginine. Other human prolactin receptor antagonists useful in the method include those in which glycine at position 129 is substituted with any of the following amino acids: valine, leucine, isoleucine, serine, threonine, proline, tyrosine, cysteine, methionine, arginine, histidine, tryptophan, phenylalanine, lysine, asparagine, glutamine, aspartic acid or glutamic acid. Any of the methods of the instant invention can be practiced with a prolactin receptor antagonist conjugated to an agent selected from the group consisting of toxins, radioactive isotopes, fluorescent dyes and proteins. In other embodiments, the methods of the present invention can be performed by administering a prolactin receptor antagonist simultaneously or sequentially with a chemotherapeutic agent. Such chemotherapeutic agents may include any of the following compounds or their combination: all-trans retinoic acid; azacitidine; azathioprine; bleomycin; carboplatin; capecitabine; cisplatin; chlorambucil; cyclophosphamide; cytarabine; daunorubicin; docetaxel; doxifluridine; doxorubicin; epirubicin; epothilone; etoposide; fluorouracil; gemcitabine; hydroxyurea; idarubicin; imatinib; mechlorethamine; mercaptopurine; methotrexate; mitoxantrone; oxaliplatin; paclitaxel; pemetrexed; teniposide; tioguanine; valrubicin; vinblastine; vincristine; vindesine and vinorelbine.

The prolactin receptor antagonist can be delivered to a patient by various routes of administration, including but not limited to: parenteral, subcutaneous, intraperitoneal, intravenous, intralymphatic, intrathecal, intraventricular or intrapulmonary. In the methods of the instant invention, a prolactin receptor antagonist can be administered prior to and/or subsequently to resection of a breast carcinoma.

The instant invention also concerns methods for localizing cancer cells in a patient's body and identifying metastasis. To accomplish this goal, a prolactin receptor antagonist conjugated to a radioactive isotope, fluorescent dye or other labeled agent is administered to a patient and the patient is then subjected to a procedure which identifies areas in which the antagonist is localized. Procedures that can be used for localizing the conjugated prolactin receptor include a computer tomography scanning procedure, a computer tomography scanning procedure, magnetic resonance imaging and nuclear magnetic resonance imaging.

DETAILED DESCRIPTION OF THE INVENTION

Figure 9:
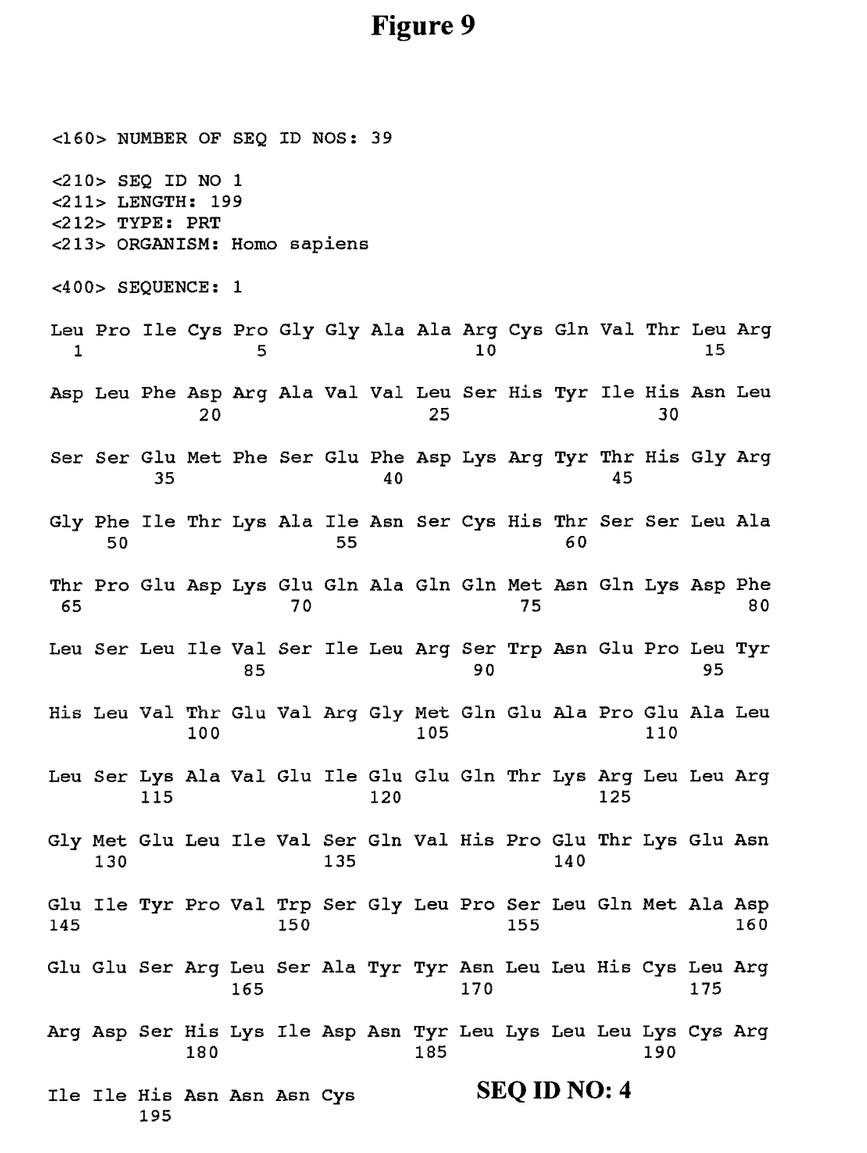
FIG. 9. Amino acid sequence of human prolactin.

The amino acid sequence for human prolactin is set forth in FIG. 9. The term "prolactin (PRL)" refers herein to human and nonhuman animal forms of the hormone prolactin (see also Cooke et al., J. Biol. Chem., 256:4007 (1981); Cooke et al., J. Biol. Chem., 225:6502 (1980); Kohmoto et al., Eur. J. Biochem., 138:227 (1984); Tsubokawa et al., Int. J. Peptide Protein Res., 25:442 (1985); Bondar et al., GenBank Accession No. #X63235 (1991); Sasavage et al., J. Biol. Chem. 257:678 (1982); Miller et al., Endocrinol. 107:851 (1980); Li et al., Arch. Biochem. Biophys. 141:705 (1970); Li, Int. J. Peptide Protein Res., 8:205 (1976); Martinant et al., Biochim. Biophys. Acta, 1077:339 (1991); Lehrman et al., Int. J. Peptide Protein Res., 31:544 (1988); Li et al., Int. J. Peptide Protein Res., 33:67 (1989); Hanks et al., J. Mol. Endocrinol., 2:21 (1989); Watahiki et al., J. Biol. Chem., 264:5535 (1989); Karatzas et al., Nucl. Acids Res., 18:3071 (1990); Yasuda et al., Gen. Comp. Endocrinol., 80:363 (1990); Noso et al., Int. J. Peptide Protein Res., 39:250; Buckbinder et al., Proc. Natl. Acad. Sci. U.S.A., 90:3820 (1993); Takahashi et al., J Mol. Endocrinol., 5:281; Yamaguchi et al., J. Biol. Chem., 263:9113 (1988); Rentler-Delrue et al., DNA, 8:261; Yasuda et al., Gen. Comp. Endocrinol., 66:280 (1987); Chang et al., GenBank Acc. No. #X61049 (1991); Chang et al., GenBank Acc. No. #X61052 (1991); Yasuda et al., Arch. Biochem. Biophys., 244:528 (1986); Kuwana et al., Agric. Biol. Chem., 52:1033 (1988); Song et al., Eur. J. Biochem., 172:279 (1988); Mercier et al., DNA 8:119 (1989)).

The term "prolactin receptor antagonist" refers to a form of prolactin that interferes with the prolactin signaling pathway. A preferred prolactin receptor antagonist comprises prolactin in which at least one amino acid is altered from its naturally occurring sequence by insertion, deletion, and/or substitution. The term G129R refers to a prolactin receptor antagonist, as for example, depictured in FIG. 9, in which glycine at position 129 is substituted with arginine.

The ability of a prolactin receptor antagonist to antagonize the action of PRL at its receptor is defined as the ability of the variant to inhibit an effect mediated by PRL. Prolactin receptor antagonists include those described in published U.S. patent application No. 2005/0271626, which is incorporated herein by reference in its entirety.

A prolactin receptor antagonist may be identified by determining the ability of a prolactin variant ("PRL variant") to block the ability of PRL to act via its receptor when both PRL and the PRL variant are present. The ability of PRL to act via its receptor can be measured via monitoring changes in cell proliferation and also as phosphorylation/activation of downstream targets in MAP-kinase and HER2/neu signaling pathways.

A prolactin variant in which a glycine residue at position 129 is replaced with another amino acid can be used in the methods of the instant invention. The substitution, represented in shorthand form by G129*, where * is a naturally occurring or synthetic amino acid other than glycine, may be the sole variation from the naturally occurring sequence or one of several alterations (including insertions, deletions, and/or substitutions of other amino acids). The substituted amino acid may be a neutral-polar amino acid such as alanine, valine, leucine, isoleucine, phenylalanine, proline, methionine; neutral non-polar amino acids such as serine, threonine, tyrosine, cysteine, tryptophan, asparagine, glutamine, aspartic acid; acidic amino acids such as aspartic or glutamic acid; and basic amino acids such as arginine, histidine or lysine. In preferred embodiments of the invention, the glycine at position 129 of hPRL may be substituted with valine, leucine, isoleucine, serine, threonine, proline, tyrosine, cysteine, methionine, arginine, histidine, tryptophan, phenylalanine, lysine, asparagine, glutamine, aspartic acid, or glutamic acid. In one embodiment of the invention, the substitution replaces the glycine at position 129 with arginine (G129R). In yet another embodiment, the present invention provides for a prolactin variant in which the glycine at position 129 is deleted.

A prolactin receptor antagonist can be linked to another protein as part of a fusion protein. For example, the prolactin antagonist may be linked to interleukin 2, green fluorescent protein, beta-galactosidase or a pore-forming protein selected from those that are described, for example, in U.S. Pat. No. 7,425,535. In yet another embodiment, a prolactin receptor antagonist is conjugated to a chemical compound. Such chemical compounds include, but are not limited to, a fluorescent dye, radioactive isotope or cell toxin such as a small molecule capable of triggering cell apoptosis.

The prolactin receptor antagonists of the invention may be prepared by chemical synthesis or by recombinant DNA techniques. Generally, a cDNA of PRL may be prepared using standard PCR amplification techniques, RNA or cDNA prepared from a cell which produces PRL (such as a pituitary cell) as a template, and oligonucleotide primers designed based on known PRL nucleic acid or amino acid sequence. A non-limiting example of the preparation of a cDNA encoding HPRL is set forth in published U.S. Pat. No. 7,115,556 (Wagner et al.). Alterations may then be introduced into the PRL cDNA either randomly or by directed mutagenesis.

Where a prolactin receptor antagonist is to be produced by recombinant techniques, a nucleic acid encoding the PRL variant may be incorporated into an expression vector, operatively linked to a suitable promoter/enhancer sequence. The expression vector may further contain one or more elements which aid in the expression of the PRL variant, including a transcription termination site, a polyadenylation site, a ribosome binding site, a signal sequence, etc. Suitable expression systems include mammalian cells, insect cells, plant cells, yeast cells, slime mold, and organisms, including transgenic plants and transgenic animals. Suitable expression vectors include herpes simplex viral based vectors such as pHSV1 (Geller et al., Proc. Natl. Acad. Sci. U.S.A. 87:8950-8954 (1990)); retroviral vectors such as MFG (Jaffee et al., Cancer Res. 53:2221-2226 (1993)), and in particular Moloney retroviral vectors such as LN, LNSX, LNCX, LXSN (Miller and Rosman, Biotechniques, 7:980-989 (1989)); vaccinia viral vectors such as MVA (Sutter and Moss, Proc. Natl. Acad. Sci. U.S.A. 89:10847-10851 (1992)); adenovirus vectors such as pJM17 (Ali et al., Gene Therapy 1:367-384 (1994); Berker, Biotechniques 6:616-624 (1988); Wand and Finer, Nature Medicine 2:714-716 (1996)); adeno-associated virus vectors such as AAV/neo (Mura-Cacho et al., J. Immunother., 11:231-237 (1992)); lentivirus vectors (Zufferey et al., Nature Biotechnology 15:871-875 (1997)); plasmid vectors such as pCDNA3 and pCDNA1 (InVitrogen), pET 11a, pET3a, pET11d, pET3d, pET22d, and pET12a (Novagen); plasmid AH5 (which contains the SV40 origin and the adenovirus major late promoter), pRC/CMV (InVitrogen), pCMU II (Paabo et al., EMBO J., 5:1921-1927 (1986)), pZipNeo SV (Cepko et al., Cell, 37:1053-1062 (1984)), pSR.alpha. (DNAX, Palo Alto, Calif.) and pBK-CMV; and baculovirus expression vectors (O'Reilly et al., BACULOVIRUS EXPRESSION VECTORS, Oxford University Press (1995)), such as p2Bac (InVitrogen).

A prolactin receptor antagonist produced in a recombinant expression system may then be purified by standard techniques, including electrophoresis, chromatography (including affinity chromatography), and ultrafiltration. A prolactin receptor antagonist can be produced as a peptide conjugated with a radioactive isotope or fluorescent dye. A biotinylated or radioactively labeled prolactin receptor antagonist can be synthesized in an in vitro transcription/translation system in which a gene for the variant is cloned into a vector under the SP6 promoter and a protein is then produced by using SP6 transcriptase and rabbit reticulocytes in the presence of biotin or radioactive label. A system for in vitro transcription/translation is commercially available from QIAGEN. Alternatively, a conjugated prolactin receptor antagonist can be produced in bacterial cells or mammalian cells which are grown in the presence of a radioactively labeled, fluorescently labeled or biotinylated amino acid. Other methods for synthesizing a labeled protein well known to a person skilled in the relevant art can also be used for producing a prolactin receptor antagonist conjugated with a radioactive isotope, fluorescent dye, paramagnetic label or biotin.

The present invention provides for methods and compositions in which a prolactin receptor antagonist may be used to inhibit proliferation of triple-negative breast cancer cells or $Her2^+$ breast cancer cells. In some embodiments, a breast cancer patient is diagnosed to determine whether her breast cancer is a triple-negative breast cancer subtype or HER2-positive subtype by means of obtaining a biopsy and staining the obtained breast cancer cells with markers that visualize whether the cancer cells express an estrogen receptor, $HER2^+$ and/or progesterone receptor. If a determination is made that the patient bears triple-negative breast cancer cells or $HER2^+$ breast cancer cells, a prolactin receptor antagonist is used to treat the patient.

To determine an effective amount of a prolactin receptor antagonist for the treatment, standard methods such as a dose-response test can be used. A patient is then treated on a daily basis with the prolactin receptor antagonist. Patient's response to the treatment can be monitored and a decrease in number of triple-negative breast cancer cells or HER2-positive cells is indicative of a positive response to the treatment. A patient may be further subjected to subsequent rounds of the treatment, depending on the need and general improvement after each round of the treatment.

The present invention also provides for methods and compositions in which a prolactin receptor antagonist may be used for treatment of ovarian, uterine (endometrial), and cervical cancers. To determine an effective amount of a prolactin receptor antagonist for the treatment, standard methods such as a dose-response test can be used. A patient may be further subjected to subsequent rounds of the treatment, depending on the need and general improvement after each round of the treatment.

The present invention also provides for methods and compositions in which a prolactin receptor antagonist is used for eradicating secondary tumor cells in a patient with metastases. In these methods, a biopsy is taken form patient's tumor during breast cancer surgery. The biopsy is then analyzed to determine whether patient's cancer subtype is triple-negative or HER2-positive. A patient is then allowed to recover from her surgery and subjected to treatment with a prolactin receptor antagonist, such as, for example, G129R for a period of two weeks. After one to two weeks, the patient is then subjected to several more rounds of the treatment. The treatment with a prolactin receptor antagonist can be administered simultaneously with other methods of treatment such as for example, chemotherapy and/or radiation.

The present invention also provides for methods and compositions in which a prolactin receptor antagonist may be used for eradicating breast cancer cells with stem cell-like characteristics. In some embodiments, a patient is subjected to treatment with a prolactin receptor antagonist as described above.

The present invention also provides for methods and compositions in which a prolactin receptor antagonist may be used for visualizing breast cancer cells with stem cell-like characteristics in a patient. In some embodiments, a prolactin antagonist is first conjugated with a detectable label such as a fluorescent dye or radioactive isotope and then administered to a patient. Localization of the antagonist in the patient is then visualized by any of the procedures known in the field. Such procedures, for example, include a computer tomography scanning procedure; magnetic resonance imaging and nuclear magnetic resonance imaging.

In the methods of the instant invention, a prolactin receptor antagonist may be administered either in a sequential or combined treatment regimen with other agents suitable for treating breast cancer. As non-limiting examples, additional agents used in a combined regimen may include a chemotherapeutic agent, an agent that inactivates the HER2/neu signaling pathway such as, for example, herceptin, anti-androgens and/or anti-estrogens, such as, for example, tamoxifen.

For therapeutic applications, the compositions of the present invention are administered to a mammal, preferably a human, in a pharmaceutically acceptable dosage form, including those that may be administered intravenously as a bolus or by continuous infusion over a period of time, by intramuscular, intraperitoneal, intracerebrospinal, subcutaneous, intra-arterial, intrasynovial, intrathecal, oral, topical, or inhalation routes. The compositions of the present invention are also suitably administered by intratumoral, peritumoral, intralesional or perilesional routes, to exert local as well as systemic effects. The intraperitoneal route is expected to be particularly useful in the treatment of various cancers and metastatic lesions.

The compositions of the present invention can be formulated according to known methods to prepare pharmaceutically useful compositions, whereby the agents of the composition are combined in an admixture with a pharmaceutically acceptable carrier vehicle. Suitable vehicles and their formulation, inclusive of other human proteins, e.g., human serum albumin, are described, for example, in REMINGTON'S PHARMACEUTICAL SCIENCES (16th ed., Osol, A., ed., Mack, Easton Pa. (1980)). To form a pharmaceutically acceptable composition suitable for effective administration, such compositions will contain an effective amount of one or more of the proteins of the present invention, together with a suitable amount of carrier vehicle. More specifically, an effective dose (amount) refers to that amount of a prolactin receptor antagonist required to inhibit proliferation of $HER2^+$ breast cancer cells or triple-negative breast cancer cells. An effective amount may be determined by using dose-response and time-response assays described in Example 8. Determining a therapeutically effective amount specifically will depend on such factors as toxicity and efficacy of the medicament. Toxicity may be determined using methods well known in the art and found in the foregoing references. Efficacy may be determined utilizing the same guidance in conjunction with the methods described below in the Examples. A pharmaceutically effective amount, therefore, is an amount that is deemed by the clinician to be toxicologically tolerable, yet efficacious. Efficacy, for example, can be measured by the decrease in mass of the targeted tumor mass.

A patient with breast cancer, ovarian cancer, uterine (endometrial) cancer or cervical cancer can be treated with a prolactin receptor antagonist composition. A patient can then be monitored for a decrease in number of cancer cells with stem-like characteristics by monitoring the decrease in ALDH1 activity in patient's cancer cells. The round of treatment with a prolactin receptor antagonist can then be repeated for further eradication of cancer cells with stem-like characteristics. In one embodiment of the instant invention, a patient can be prescribed from 1 to 6 rounds of the treatment, each round consisting of 1 to 10 days.

A prolactin receptor antagonist may be used for visualizing breast cancer, ovarian, uterine (endometrial) or cervical cancer cells with stem-like characteristics. In one embodiment, a prolactin receptor antagonist can be administered as a fusion with a green fluorescent protein. In other embodiments, a prolactin receptor antagonist is conjugated with a fluorescent dye or radioactive isotope and administered to a patient. The patient is then monitored for localization of the prolactin receptor antagonist in her body.

The compositions for use in accordance with the present invention may be formulated in conventional manner using one or more physiologically acceptable carriers or excipients. Thus, they may be formulated for administration by inhalation or insufflation (either through the mouth or the nose) or oral, buccal, parenteral or rectal administration.

Preparations for oral administration may be suitably formulated to give a controlled release of an active compound. For buccal administration the composition may take the form of tablets or lozenges formulated in conventional manner. For administration by inhalation, the compositions according to the present invention are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of, e.g. gelatin for use in an inhaler or insufflator may be formulated containing a powder mix of the compound and a suitable powder base such as lactose or starch.

The compositions of the present invention may be formulated for parenteral administration by injection, e.g., by bolus injection or continuous infusion. Formulations for injection may be presented in unit dosage form, e.g., in ampules or in multi-dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen-free water, before use. The composition may also be formulated in rectal compositions such as suppositories or retention enemas, e.g., containing conventional suppository bases such as cocoa butter or other glycerides. In addition to the formulations described previously, the compositions of the present invention may also be formulated as a depot preparation. Such long acting formulations may be administered by implantation (for example subcutaneously or intramuscularly) or by intramuscular injection. Thus, for example, the prolactin variant and/or agent that inactivates the HER2/neu signaling pathway may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack or dispenser device may be accompanied by instructions for administration.

Furthermore, the compositions of the present invention can also be modified to have a longer clearance rate and therefore increase bioavailability by protecting the composition from an immune response and other clearance mechanisms afforded by the subject. For example, PEGylated compounds exhibit reduced immunogenicity and antigenicity, and circulate in the bloodstream considerably longer than unconjugated proteins. PEG (polyethylene glycol) polymer chains can be attached to the prolactin variant/prolactin receptor antagonist by methods known in the art, such as by the PEGylation procedure described in Roberts et al., Adv. Drug Del. Rev., 54(4):459-76 (2002). But other agents which can prolong elimination half-life of the therapeutic composition of the present invention are known to the skilled artisan and contemplated herein.

In fact, the compositions described herein can also be modified with hydroxyethylstarch (HES). HES is a derivative of naturally occurring amylopektine and is degraded by alpha-amylase in the body. Methods for making HES-protein conjugates are known in the art. See, for example, EP 1398322, DE 2616086 and DE 2646854.

Agents that link a prolactin receptor antagonist to serum albumin are also contemplated in the present invention to prolong clearance time and increase half-life of the inventive composition. While such agents are disclosed in US Patent Publication 2007/0160534, which is incorporated herein by reference, other peptide ligands which have an affinity for serum albumin that can be conjugated to the prolactin receptor antagonist of the present invention are also considered suitable for use herein.

The invention is further described by reference to the following examples, which are provided for illustration only. The invention is not limited to the examples but rather includes all variations that are evident from the teachings provided herein.

Example 1

Preparation of Human Prolactin Antagonist G129R

Human PRL was successfully cloned using reverse transcription (RT) followed by polymerase chain reaction (PCR). Briefly, human pituitary polyA RNA (CloneTech, Inc. Palo Alto, Calif.) was used as template. A HPRL antisense primer was designed starting 2 bases from the stop codon (TAA) of hPRL cDNA (5'-GCTTAGCAGTTGTTGTTGTG-3; SEQ ID NO: 1) and a sense primer was designed from ATG (5'-ATGAACATCAAAGGAT-3; SEQ ID NO: 2). RT/PCR was carried out using a kit from Perkin-Elmer Cetus, Inc. (Norwalk, Conn.). The nucleotide sequence of the resulting hPRL was determined by the dideoxy chain-termination method using modified T7 DNA polymerase (Sequenase, United States Biochemical), and was found to be identical to that reported in GenBank except for a one base difference which results in a silent mutation at codon 21 (CTG→CTC). A schematic representation of the cloning process, including preparation of the pUCIG-Met expression vector, is summarized in published US Patent Application No. 2003 0022833 (Wagner et al.), which is incorporated herein by reference in its entirety.

The parental plasmid which contains the hPRL cDNA and a M13 F1 origin of replication was transformed into *E. coli* (CJ236). Single stranded plasmid DNA containing uridine was isolated from the transformed CJ236 bacteria using the helper bacteriophage, M13k07. Six pmol of oligonucleotide containing sequence directing the G129R mutation was annealed with 0.2 pmol of single stranded DNA in annealing buffer (200 mM Tris-HCl, 20 mM $MgCl_2$, 100 mM NaCl) by heating to 70° C. for 5 minutes followed by slow cooling. The oligonucleotide (5'-CGGCTCCTAGAGAG-GATGGAGCT-3'; SEQ ID NO: 3), which encodes the G129R mutation was used to prime synthesis of a complementary strand of DNA, using single stranded DNA as a template, that is catalyzed by T4 DNA polymerase. After synthesis, the double stranded DNA was used to transform *E. coli* (DH5a). Individual clones were isolated and screened for hPRL-G129R by DNA nucleotide sequencing.

The hPRL and G129R encoding nucleic acids were each inserted into a mammalian cell expression vector in which transcription of the cDNAs is controlled by the mouse metallothionein enhancer/promoter sequence and bGH poly A addition signal (Chen et al., J. Biol. Chem., 266:2252-2258 (1991); Chen et al., Endocrinol., 129:1402-1408 (1991); Chen et al., Mol. Endocrinol., 5:1845-1852 (1991); Chen et al., J. Biol. Chem., 269:15892-15897 (1994)). To establish stable mouse L cell lines which produce hPRL and hPRLA, mouse L cells [thymidine kinase-negative (TK) and adenine phosphoribosyl transferase-negative (APRT)] were selected as an in vitro expression system. Stable cell lines which express HPRL (which will be used as positive control) and human prolactin antagonist (about 5-10 mg/1/24 h/million cells) were prepared.

Membrane ultrafiltration was used to partially purify as well as concentrate hPRL and human prolactin antagonist from conditioned cell culture media, using techniques as set forth in Chen et al., J. Biol. Chem. 269:15892-15897 (1994). The separation is based on the relative molecular size and the pore size of membrane. The ultrafiltration membranes were obtained from Amicon, Inc. (Northorough, Mass.). Two types of membranes were used, YM10 and YM100. A 200 ml stirred cell with Amicon YM100 under 20 psia transmembrane pressure was first used for removal of large impurities from the culture media. The permeate (>90% of recovery of hPRL) was applied onto a second filtration protocol which uses YM10 membrane to reduce the volume of solution and thus concentrate the protein. The concentration of HPRL or human prolactin antagonist was determined using an immunoradiometric assay (IRMA) kit from Diagnostic Products Corp. (Los Angeles, Calif.).

Example 2

Treatment of Triple-Negative Breast Cancer Cells with Prolactin Receptor Antagonist G129R Results in the Decreased ALDH1 Activity in the Cells Human triple-negative breast cancer cells MDA-MB-231 and control breast cancer cells T-47D were plated in 6 well plates at $1 \times 10^5$ cells/ml, and allowed to adhere for 24 hours in growth media followed by 2 hours of serum free media depletion. The cells were then cultured either without (control) or with prolactin (100 ng/ml) or G129R (10 ug/ml) for three days. The cells were then collected and the ALDH-1 activity (this enzyme is a marker for cancer stem cells. See Ginestier et al., Cell Stem Cell 2007 1(5): 555-567) was measured by ALDEFLUOR® fluorescent assay (StemCell Technologies).

Figure 1:
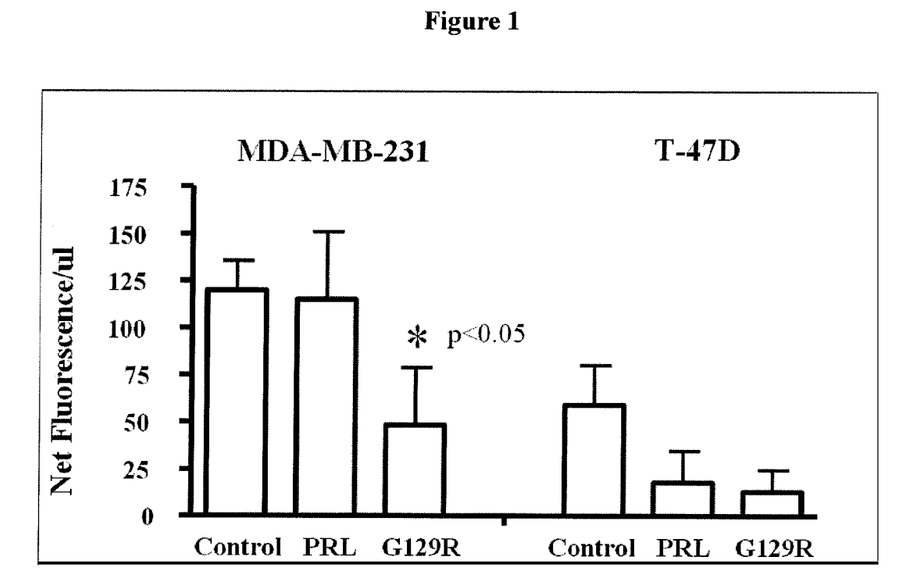
FIG. 1. Treatment of triple-negative breast cancer cells with prolactin receptor antagonist G129R results in the decreased ALDH1 activity.

As shown in FIG. 1, treatment with prolactin antagonist G129R significantly reduced the ALDH1 activity in triple-negative breast cancer cells.

Example 3

Figure 2:
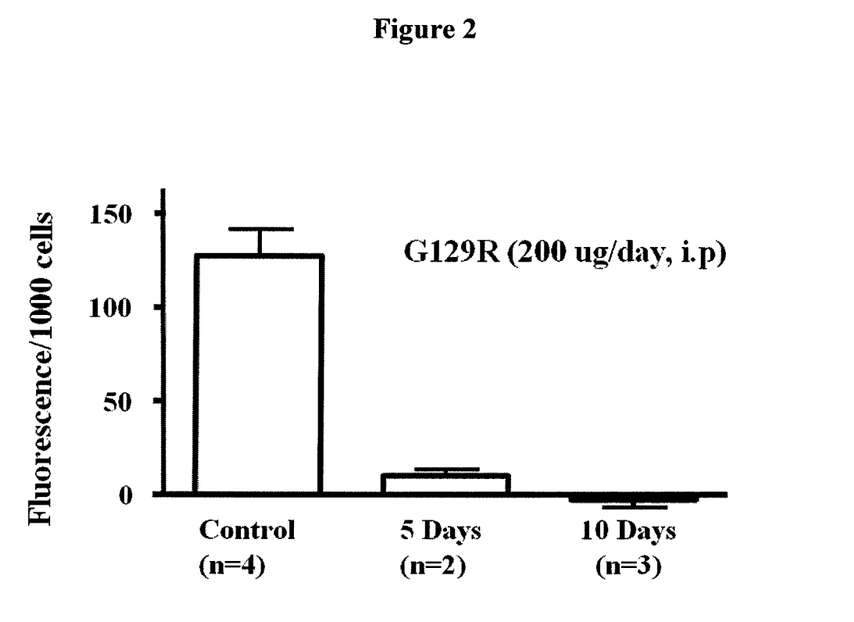
FIG. 2. Treatment of mice bearing HER2+/neu breast tumors with prolactin receptor antagonist G129R reduces the ALDH1 activity in the tumor cells.

Treatment with Prolactin Receptor Antagonist Reduces the ALDH1 Activity in Tumor Cells MMTV/neu transgenic mice carry an activated c-neu oncogene driven by a mouse mammary tumor virus (MMTV) promoter and develop mammary HER2$^+$ adenocarcinomas (Muller et al. 1988. Cell. 54(1):105-15). MMTV/neu transgenic mice bearing mammary tumors were treated with PBS (n=4) or G129R for 5 (n=2) or 10 (n=3) days (10 mg/kg, i.p.). The tumors were isolated at the end of treatment, digested to a single cell suspension, and ALDH1 activity levels were compared. As can be seen from FIG. 2, the ALDH1 activity was significantly reduced in cancer cells isolated from animals treated with G129R. Practically no ALDH1 activity was detected in cancer cells that were treated with G129R for ten days.

Example 4

Figure 3:
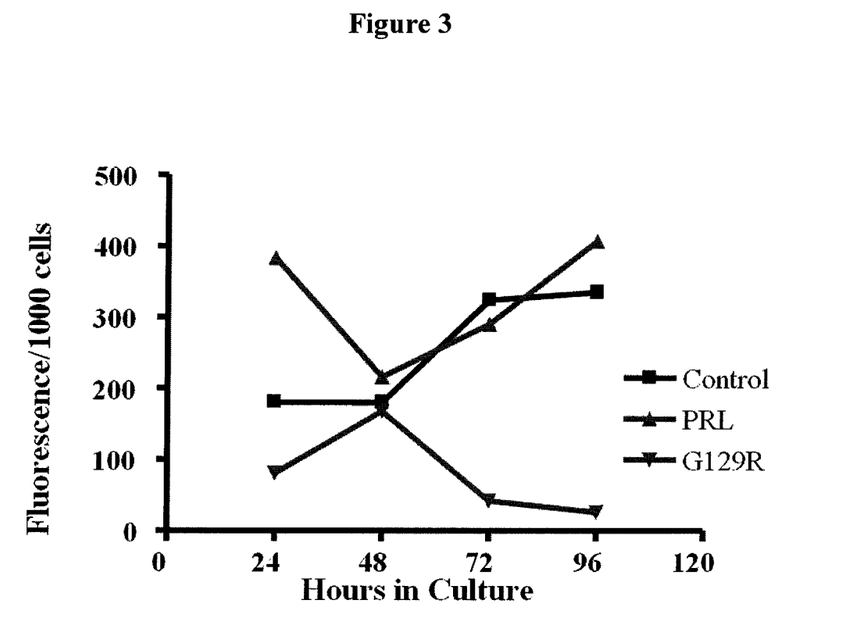
FIG. 3. Treatment of primary HER2+/neu breast cancer cells with prolactin receptor antagonist G129R results in the decreased ALDH1 activity.

Treatment of Cancer Cells with Prolactin Receptor Antagonist Results in the Decreased ALDH1 Activity Primary mammary tumor cells were isolated from MMTV/neu transgenic mouse and cultured in the presence of G129R (10 ug/ml) or PRL (100 ng/ml) for 24, 48, 72, or 96 hrs. Specifically, tumor removed from an MMTV-neu mouse was digested to a single cell suspension and plated in 12-well plates at 1×10$^5$ cells/ml. Cells were allowed to adhere for 24 hours in growth media followed by 2 hours of serum-free media depletion. The cells were then either treated without (control) or with prolactin (100 ng/ml) or G129R (10 ug/ml). Cells were collected following 24, 48, 72, or 96 hours of treatment and the ALDH-1 activity was measured. As can be seen from FIG. 3, the time course study of the primary MMTV/neu tumor cells exposed to G129R revealed a steady decrease in ALDH1 activity, with final levels significantly lower than that of a control (92.3% reduction at 96 hrs).

Example 5

Prolactin Antagonist Inhibits Development of Metastases in Mammals

Figure 4:
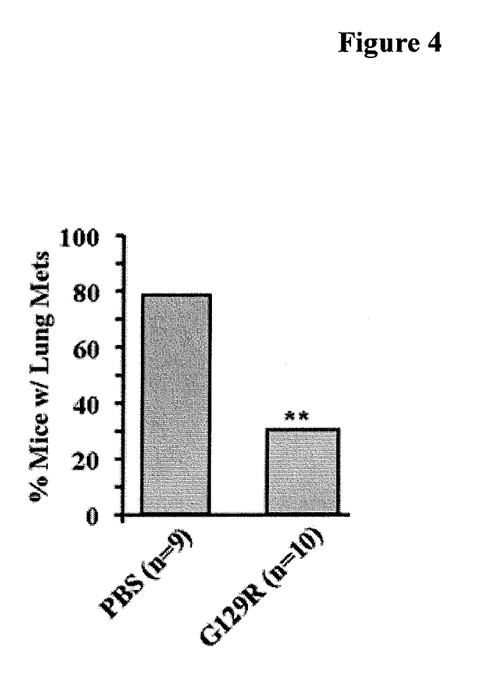
FIG. 4. Prolactin antagonist G129R inhibits development of metastases in mammals with HER2+/neu breast tumors.

Primary breast tumors were removed from MMTV/neu transgenic mice. The mice were then treated either with PBS or G129R (200 ug/day, i.p.) for more than 40 days. When the secondary tumors (recurrence) grew to a certain size, the mice were sacrificed and the lungs were excised and fixed in Bouin's fixative to observe metastasis. FIG. 4 shows percentages of animals with lung metastases in the G129R treated and control groups (a Chi-squared test was utilized to determine significance). As can be seen from FIG. 4, the percentage of animals with lung metastases in the G129R treated group was significantly reduced in comparison to the untreated control group ** ($P<0.05$).

Example 6

Prolactin Antagonist Suppresses Growth of Tumors in Mammals

Figure 5:
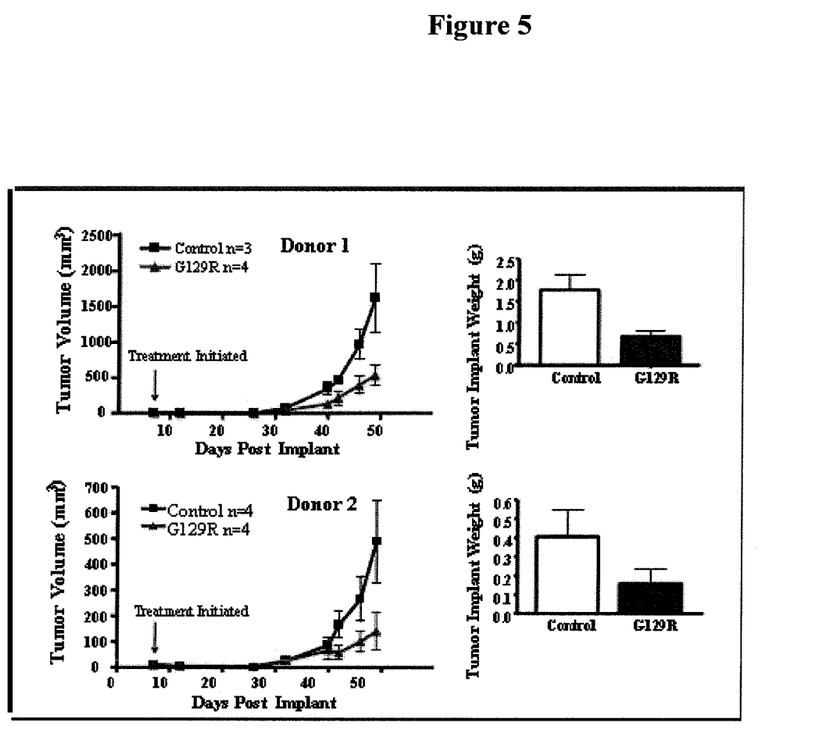
FIG. 5. Prolactin antagonist G129R suppresses growth of HER2+/neu tumors in mammals.

In two separate experiments, tumors were isolated from female transgenic mice, sectioned into equivalent sized pieces and implanted into age-matched recipient female transgenic mice. Ten days after implantation, mice were randomized into either control (n=3-4) or G129R treated groups (n=4, 10 mg/kg, i.p. daily). The mice were then treated on a daily basis for 50 days and tumor volumes for the control and treated groups were monitored. As shown in FIG. 5, final tumor volumes were 67.1% (±9.18 SEM) or 71.5% (±14.9 SEM) smaller in two G129R treated groups as compared to control groups. As also shown in FIG. 5, final tumor weights were reduced by 61.3% (±18.4 SEM) or 62.5% (±7.07 SEM) in G129R treated groups in comparison to control groups.

Example 7

Figure 6:
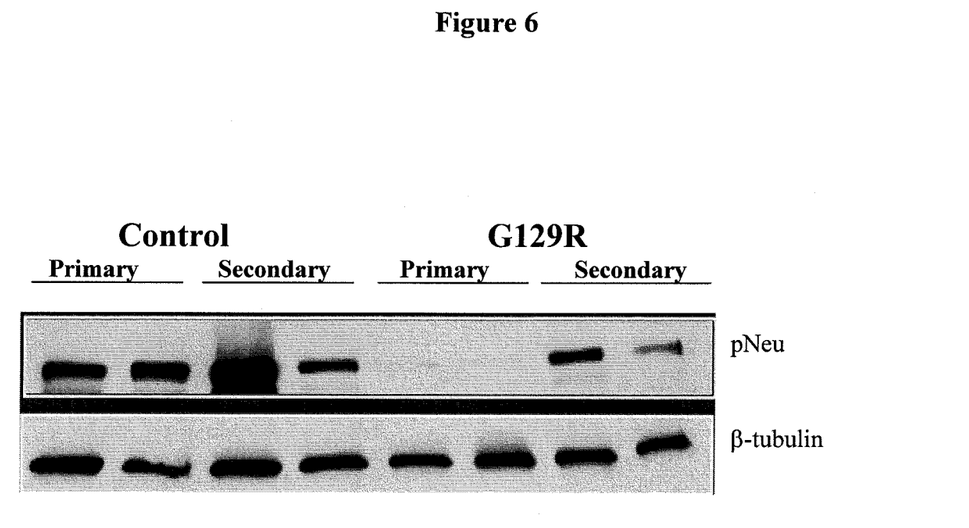
FIG. 6. Treatment with prolactin antagonist G129R suppresses phosphorylation of HER2+/neu protein in primary and secondary tumors in mammals.

Treatment with Prolactin Antagonist Suppresses Phosphorylation of HER2$^+$/Neu Protein in Primary and Secondary Tumors in Mammals MMTV/neu mice (bearing primary and secondary tumors) were treated either with PBS (control) or with 200 ug of G129R per day for 5 days. Primary and secondary tumors were removed 24 hours following the 5th treatment and processed for western blotting. As shown in FIG. 6, there was a significant decrease in phosphorylated Neu protein in primary tumors isolated from animals treated with G129R. The secondary tumors from G129R treated animals also showed a decrease in phosphorylation of neu. However, some phosphorylated neu protein was still detected in the secondary tumors of the G129R treated mice (see FIG. 6), suggesting that treatment with prolactin antagonist G129R may affect primary and secondary tumors differently.

Example 8

Figure 7:
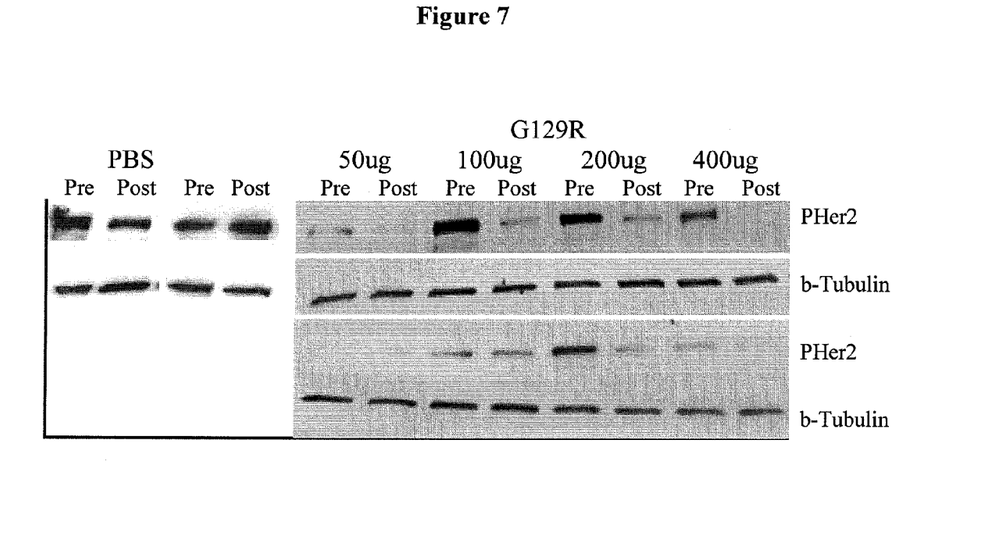
FIG. 7. Dose-dependent response of HER2+ tumors in vivo to treatment with prolactin antagonist G129R.

Dose-Dependent Response of HER Tumors In Vivo to Treatment with Prolactin Antagonist G129R and Time-Dependent Response of HER$^+$ Tumors In Vivo to Treatment with Prolactin Antagonist G129R To determine a minimal dosage of G129R required for decreasing phosphorylation of HER$^+$/neu in vivo, a biopsy was removed from tumors of MMTV/neu transgenic mice and was used as a self-control baseline. The mice were then treated i.p. for ten days with either PBS or G129R at the following concentrations: 50, 100, 200 or 400 ug daily (2.5 mg/kg/day, 5 mg/kg/day; 10 mg/kg/day; or 20 mg/kg/day of G129R). The tumors were then harvested and processed for western blotting. The western blots were then probed with an antibody that detects phosphorylated HER2/neu protein and an antibody against beta-tubulin as a control for gel loading and western blotting transfer. As can be seen from FIG. 7, the inhibitory effect of G129R on phosphorylation of HER$^+$/neu was observed at a dosage of G129R as low as 5 mg/kg/day.

Figure 8:
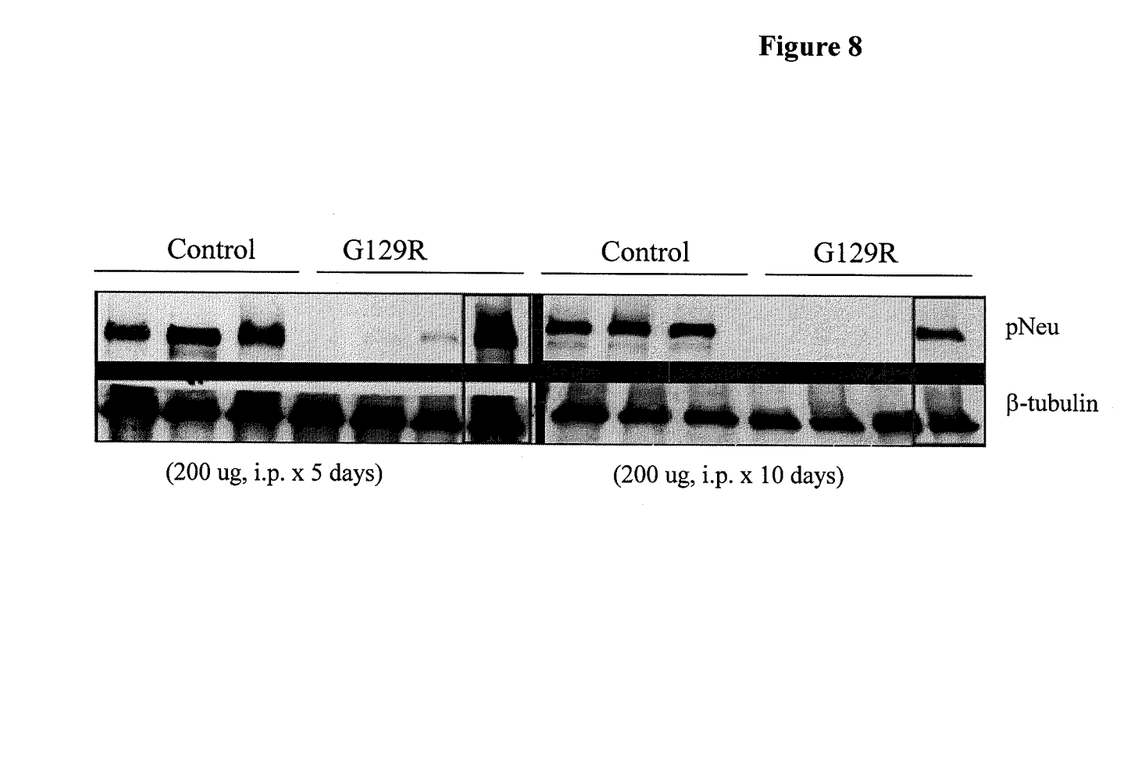
FIG. 8. Time-dependent response of HER+ tumors in vivo to treatment with prolactin antagonist G129R.

To determine an optimal length of treatment with G129R, MMTV tumor-bearing mice were treated with 200 ug G129R for either five or ten days. Tumors were removed 24 hours after the last treatment and processed for western blot analysis. As can be seen in FIG. 8, of 14 mice receiving a 5 day treatment of G129R (10 mg/kg/day, i.p.), tumors from 5 mice showed drastic reduction in the phosphorylated HER2/neu protein as compared to control mice (n=8), 4 were moderate responsive with noticeable reduction in phosphorylated HER2/neu protein and 5 were nonresponsive. As also can be seen in FIG. 8, of 10 mice receiving a 10 day treatment of G129R (10 mg/kg/day, i.p.), tumors from 3 mice were highly responsive and virtually no phosphorylated HER2/neu was detected in these tumors, 5 mice were moderately responsive and 2 mice were nonresponsive.

SEQUENCE LISTING

<160> NUMBER OF SEQ ID NOS: 4

<210> SEQ ID NO 1
<211> LENGTH: 20
<212> TYPE: DNA
<213> ORGANISM: Artificial
<220> FEATURE:
<223> OTHER INFORMATION: Synthetic oligonucleotide

<400> SEQUENCE: 1
gcttagcagt tgttgttgtg                                          20

<210> SEQ ID NO 2
<211> LENGTH: 16
<212> TYPE: DNA
<213> ORGANISM: Artificial
<220> FEATURE:
<223> OTHER INFORMATION: Synthetic oligonucleotide

<400> SEQUENCE: 2
atgaacatca aaggat                                              16

<210> SEQ ID NO 3
<211> LENGTH: 23
<212> TYPE: DNA
<213> ORGANISM: Artificial
<220> FEATURE:
<223> OTHER INFORMATION: Synthetic oligonucleotide

<400> SEQUENCE: 3
cggctcctag agaggatgga gct                                      23

<210> SEQ ID NO 4
<211> LENGTH: 199
<212> TYPE: PRT
<213> ORGANISM: Homo sapiens

<400> SEQUENCE: 4

Leu Pro Ile Cys Pro Gly Gly Ala Ala Arg Cys Gln Val Thr Leu Arg
1               5                   10                  15

Asp Leu Phe Asp Arg Ala Val Val Leu Ser His Tyr Ile His Asn Leu
            20                  25                  30

Ser Ser Glu Met Phe Ser Glu Phe Asp Lys Arg Tyr Thr His Gly Arg
        35                  40                  45

Gly Phe Ile Thr Lys Ala Ile Asn Ser Cys His Thr Ser Ser Leu Ala
    50                  55                  60

Thr Pro Glu Asp Lys Glu Gln Ala Gln Gln Met Asn Gln Lys Asp Phe
65                  70                  75                  80

Leu Ser Leu Ile Val Ser Ile Leu Arg Ser Trp Asn Glu Pro Leu Tyr
                85                  90                  95

His Leu Val Thr Glu Val Arg Gly Met Gln Glu Ala Pro Glu Ala Leu
            100                 105                 110

Leu Ser Lys Ala Val Glu Ile Glu Glu Gln Thr Lys Arg Leu Leu Arg
        115                 120                 125

Gly Met Glu Leu Ile Val Ser Gln Val His Pro Glu Thr Lys Glu Asn
    130                 135                 140

Glu Ile Tyr Pro Val Trp Ser Gly Leu Pro Ser Leu Gln Met Ala Asp
145                 150                 155                 160

Glu Glu Ser Arg Leu Ser Ala Tyr Tyr Asn Leu Leu His Cys Leu Arg
                165                 170                 175

```
Arg Asp Ser His Lys Ile Asp Asn Tyr Leu Lys Leu Leu Lys Cys Arg
            180                 185                 190

Ile Ile His Asn Asn Asn Cys
            195
```

The invention claimed is:

1. A method for inhibiting growth of cancer cells in a patient, comprising administering to the patient an effective amount of a human prolactin receptor antagonist comprising the sequence of SEQ ID NO: 4 in which a glycine residue at position 129 is substituted with another amino acid;
wherein the cancer cells do not express estrogen receptor, progesterone receptor and HER2/neu; and further wherein the cancer cells are selected from the group consisting of ovarian cancer cells, uterine (endometrial) cancer cells, cervical cancer cells and breast carcinoma cells.

2. A method for inhibiting metastases of the cancer cells of claim 1 in a patient, comprising administering to the patient an effective amount of a human prolactin receptor antagonistantagonist comprising the sequence of SEQ ID NO: 4 in which a glycine residue at position 129 is substituted with another amino acid.

3. A method for decreasing the activity of aldehyde dehydrogenase 1 (ALDH1) of the cancer cells of claim 1 in a patient, comprising administering to the patient an effective amount of human prolactin receptor antagonist comprising the sequence of SEQ ID NO: 4 in which a glycine residue at position 129 is substituted with another amino acid.

4. A method for decreasing the number of cancer stem cells in the cancer cells of claim 1 in a patient, comprising administering to the patient an effective amount of a human prolactin receptor antagonist comprising the sequence of SEQ ID NO: 4 in which a glycine residue at position 129 is substituted with another amino acid.

5. The method of claim 1, wherein the human prolactin receptor antagonist G129R is human prolactin in which a glycine residue at position 129 is substituted with arginine.

6. The method of claim 1, 2, 3 or 4 wherein the glycine residue at position 129 of SEQ ID NO: 4 is substituted with an amino acid selected from the group consisting of valine, leucine, isoleucine, serine, threonine, proline, tyrosine, cysteine, methionine, arginine, histidine, tryptophan, phenylalanine, lysine, asparagine, glutamine, aspartic acid and glutamic acid.

7. The method of claim 1, 2, 3, or 4, wherein the prolactin receptor antagonist is G129R.

8. The method of claim 1, wherein the human prolactin receptor antagonist is conjugated to an agent selected from the group consisting of toxins, radioactive isotopes and fluorescent dyes.

9. The method of claim 1, wherein the human prolactin receptor antagonist is administered simultaneously or sequentially with a chemotherapeutic agent.

10. The method of claim 1, 2, 3, or 4, wherein the human prolactin receptor antagonist is administered by a route selected from the group consisting of parenteral, subcutaneous, intraperitoneal, intravenous, intralymphatic, intrathecal, intraventricular or intrapulmonary administration.

11. The method of claim 1, wherein the human prolactin receptor antagonist is administered subsequently to resection of cancer.

* * * * *